United States Patent [19]

Bischoff

[11] Patent Number: 5,012,802
[45] Date of Patent: May 7, 1991

[54] ATHLETIC PROTECTOR

[76] Inventor: Linda L. Bischoff, Box 174, Celista, B.C., Canada, U0E 1L0

[21] Appl. No.: 457,880

[22] Filed: Dec. 27, 1989

[51] Int. Cl.⁵ .................................................. A61F 5/40
[52] U.S. Cl. ..................................... 128/158; 128/159
[58] Field of Search ............................... 128/157-162, 128/98.1, 96.1, 891, 883

[56] References Cited

U.S. PATENT DOCUMENTS

| | | | |
|---|---|---|---|
| 2,408,723 | 10/1946 | Arpin et al. | 128/158 |
| 2,982,968 | 5/1961 | Groot | 2/22 |
| 3,664,336 | 5/1972 | Gelston | 128/158 |
| 3,880,160 | 4/1975 | Hall | 128/158 |
| 4,186,739 | 2/1980 | Hall et al. | 128/158 |
| 4,294,238 | 10/1981 | Woodford | 2/22 X |
| 4,453,541 | 6/1984 | Castelli et al. | 128/158 |
| 4,622,962 | 11/1986 | Kauffman | 128/160 X |
| 4,660,554 | 4/1987 | Wright | 128/158 |

FOREIGN PATENT DOCUMENTS 3664 5/1989 World Int. Prop. O. .......... 128/158

Primary Examiner—Robert A. Hafer
Assistant Examiner—Kevin G. Rooney
Attorney, Agent, or Firm—Stanley E. Johnson

[57] ABSTRACT

An athletic protector wherein the harness has a split detachably connectable waistband whereby the jock strap may be put on or taken off by the wearer without the need to completely undress. The harness has a front and rear panel merging one into the other by a narrower crotch portion with each of opposite marginal edges of the panels having a band of elastic or stretchable material secured thereto. On the inside of the front panel of the harness there is an open pouch, removably to receive a protective cup that is selectively adjustable in size and/or curvature. The opening to the pouch is preferably on the side so that the cup is slid in from the side. The opening to the pouch can be closed by a velcro type or button fastener or the equivalent.

8 Claims, 4 Drawing Sheets

ATHLETIC PROTECTOR

FIELD OF INVENTION

This invention relates generally to athletic protectors and more particularly to improvements in the harness (also referred to herein as a jock strap) of an athletic protector; to protector cup adjustably variable in size and/or curvature; to an athletic harness or jock strap having a pouch for the removable insertion of a protective cup and to combinations and sub-combinations of the foregoing.

BACKGROUND OF INVENTION

An athletic protector with a removable, rigid, cup of fixed size is known from the teachings of U.S. Pat. No. 3,782,375 issued Jan. 1, 1974 to D. W. Donars. In the patented structure, the rigid cup is detachably mountable on the jock strap support or harness, by way of Velcro hook and loop fasteners or strips having portions strategically located and mounted on the rigid cup and further portions strategically located and mounted on the jock strap. The patentee has indicated that other detachable means may be employed for example, snap fasteners, zipper components and any other types of conventional fasteners.

In an attempt to improve the comfort of an athletic support, J. V. Rotello in his U.S. Pat. No. 3,963,022 issued June 15, 1976 discloses using a single piece elastic waistband. The purpose is so that the waistband will seek its own proper position on the wearers body for maximum comfort and at the same time, provide adjustability to accommodate both long and short torsos, as well as broad and thin torsos. An elastic waistband, with Velcro fasteners in the harness of a penal support is disclosed in U.S. Pat. No. 4,622,962 issued Nov. 18, 1986 to R. D. Kauffman.

SUMMARY OF INVENTION

A principle object of the present invention is to provide a protective athletic support for use by both males and females; one which can be put on or taken off without completely undressing; and one which is comfortable to use.

In keeping with the foregoing, there is provided in accordance with one aspect of the present invention an athletic support comprising fabric front and rear panels separated one from the other by a narrow crotch portion that passes between the wearers legs, said front panel having a front marginal end and said rear panel have a rear marginal end. The front and rear panels have opposite marginal edges, extending from one of said ends to the other and which are made of a stretchable or elastic material. First and second portions of an elastic waistband are secured respectively to the front and rear marginal ends of the panels and means detachably connects adjacently disposed ends of the waistband portions thus providing a selectively adjustable variable sized waistband that can be easily opened, allowing one to put the harness on or take it off without completely undressing. The waistband is preferably a four inch elastic at the top of front and back panels which provides a good back and stomach support. Also, it makes for a sturdier garment which enables straps and fastenings to hold up socks better, i.e. a hockey garment. A pouch is provided on the front panel and it has an open edge portion for removably inserting a rigid protective cup into the pouch. The pouch, although it could be on the outside, is on the inside of the garment next to the wearer's body and has the access opening on the side thereof.

In accordance with a further aspect of the present invention, there is provided a jock strap having a front panel, a pouch on said front panel with an open edge portion for removably receiving therein a rigid protective cup and a rigid protective cup, said rigid protective cup comprising first and second shell like portions detachably interconnected at different selected positions selectively to vary the longitudinal extent and/or curvature of the cup.

LIST OF DRAWINGS

The invention as illustrated by way of example in the accompanying drawings wherein.

DESCRIPTION OF PREFERRED EMBODIMENT

Figure 1:
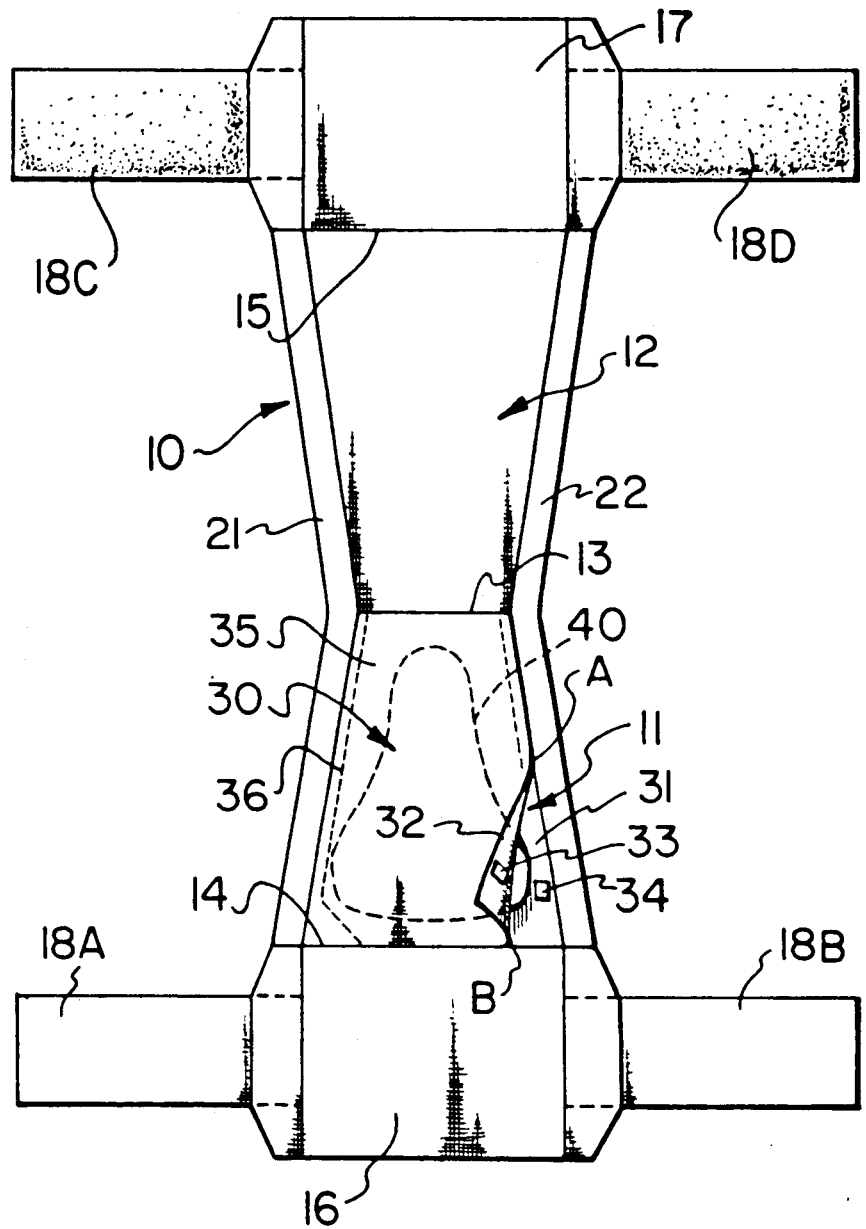
FIG. 1 is a plan view of the inside of a jock strap provided in accordance with the present invention, laid out flat.

In the drawings there is illustrated an athletic support harness or jock strap 10 having respective front and rear panel portions 11 and 12, joined one to the other by a narrow crotch portion 13 that passes between the wearers legs. The panels 11 and 12 have respective opposite ends designated 14 and 15, to which there is attached respective elastic waistband portions 16 and 17. Each of the waistband portions have means on opposite ends thereof, for example velcro strips, for joining one waistband portion to the other providing a closed stretchable waistband that is adjustably variable in size. This adjustment permits the wearer to adjust the tension of the elastic band around his or her waist. The front elastic waistband portion 16 has velcro bands 18A and 18B extending from opposite ends thereof and similarly the rear waistband portion 17 has velcro bands 18C and 18D extending from opposite ends thereof.

The front and rear panels 11 and 12 are preferably a continuous piece of fabric and are preferably made from an interlock knit cloth. The outside of the front and rear panels could, if desired, be ski wear type nylon and suitably lined, if desired, as aerobic knit consisting of 45% cotton, 45% polyester and 10% lycra or 85% nylon, 15% lycra. The choice of material will be obvious to those skilled in the art. Opposite edges of the panels, designated respectively 21 and 22, are made of a stretchable material for example, stretch type fabric or elastic bands attached to the cloth.

Figure 2:
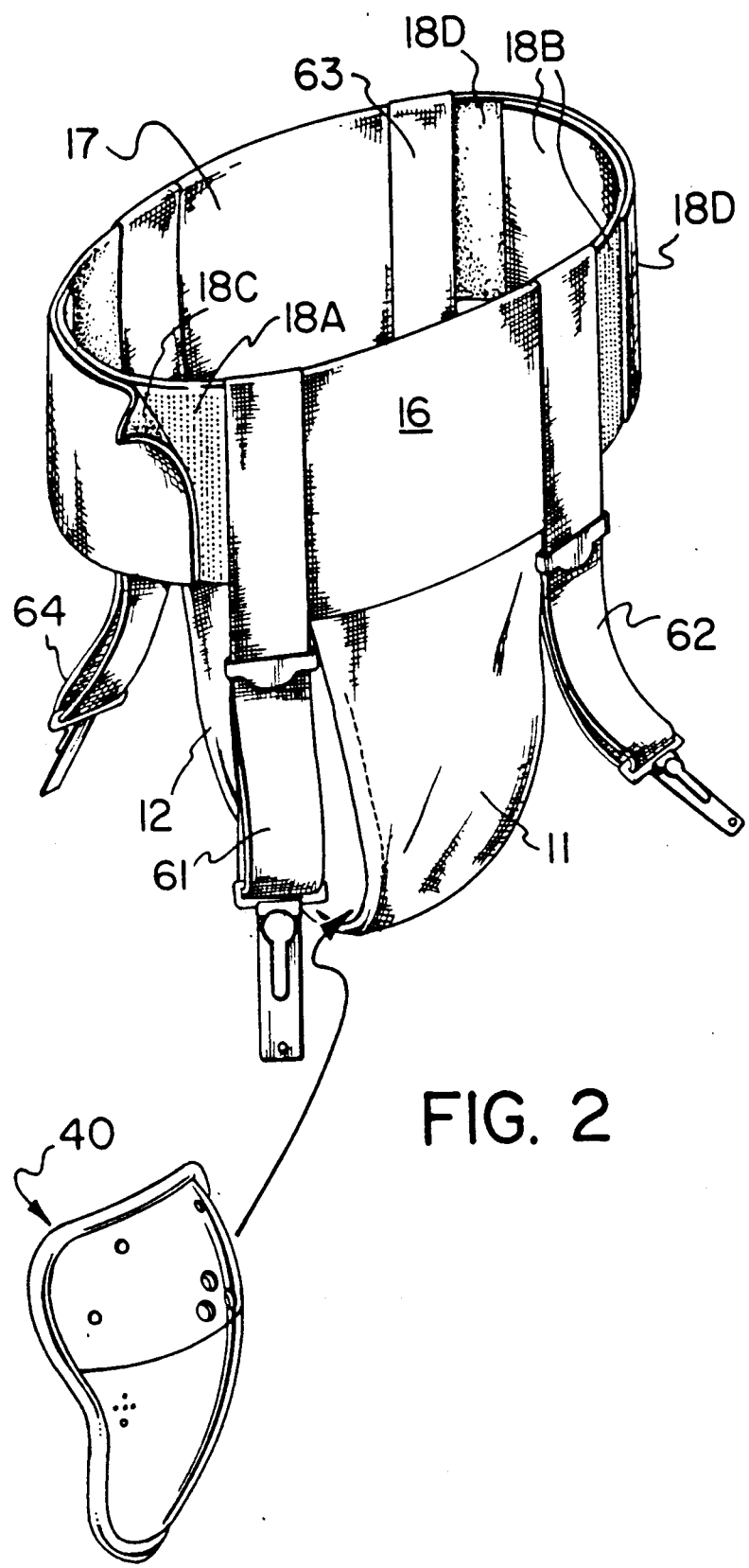
FIG. 2 is an oblique view of a jock strap in a wearing position with garter straps attached but with the protective cup removed from the pocket.
Figure 4:
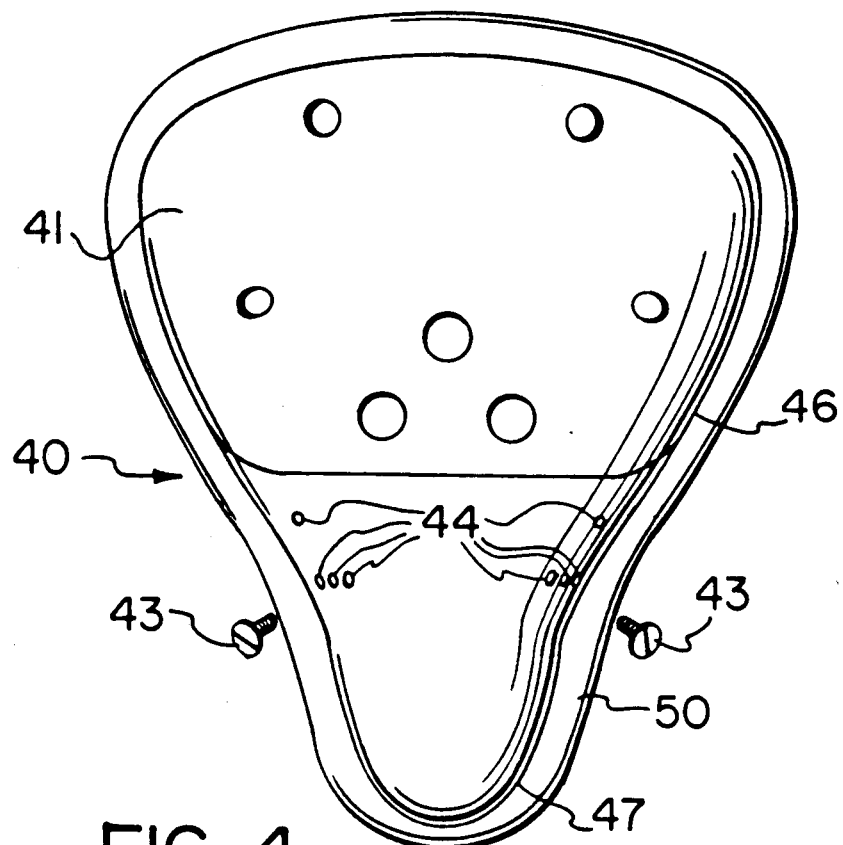
FIG. 4 is a front view of an athletic support protective cup, provided in accordance with the present invention.
Figure 5:
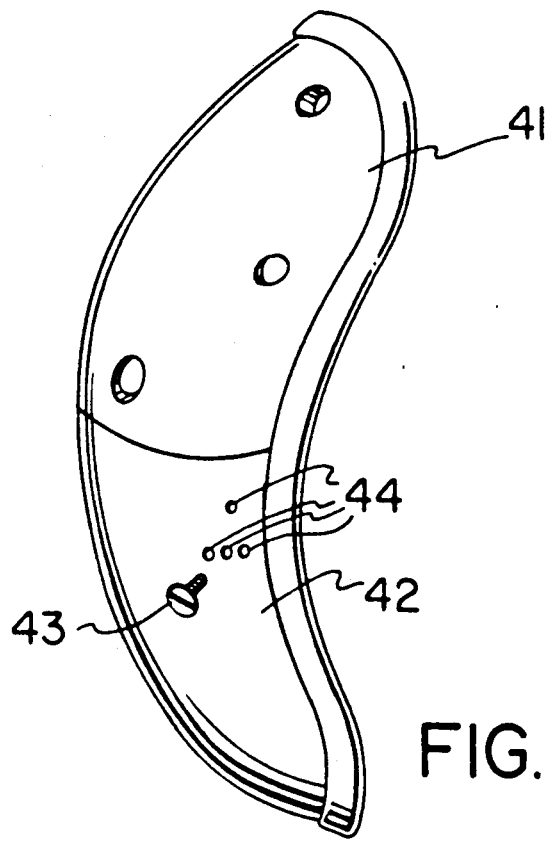
FIG. 5 is a side oblique view of the cup illustrated in FIG. 4.

The front panel 12 is provided with a pouch 30 that has an access opening 31 for removable insertion thereinto of a protective cup 40. The access opening results in a flap 32, that fastens to the front panel by co-operating velcro pieces 33 and 34. The cup 40 is shown in broken line in FIG. 1 and a preferred form of the same cup is illustrated in FIGS. 4 and 5. In FIG. 2 the protective cup is shown removed from the pouch.

The pouch 30 can be a separate piece of material 35 stitched along seam 36 to the front panel, except for a gap from points designated A and B. This unstitched gap, from A to B, provides the previously defined access opening 31 for insertion of the protective cup into the pouch. Alternatively the front panel can be multi-layered with stitching joining the layers to define a pocket or pouch and a slit in the inside (or outside if desired) layer provide a pouch access opening.

Figure 3:
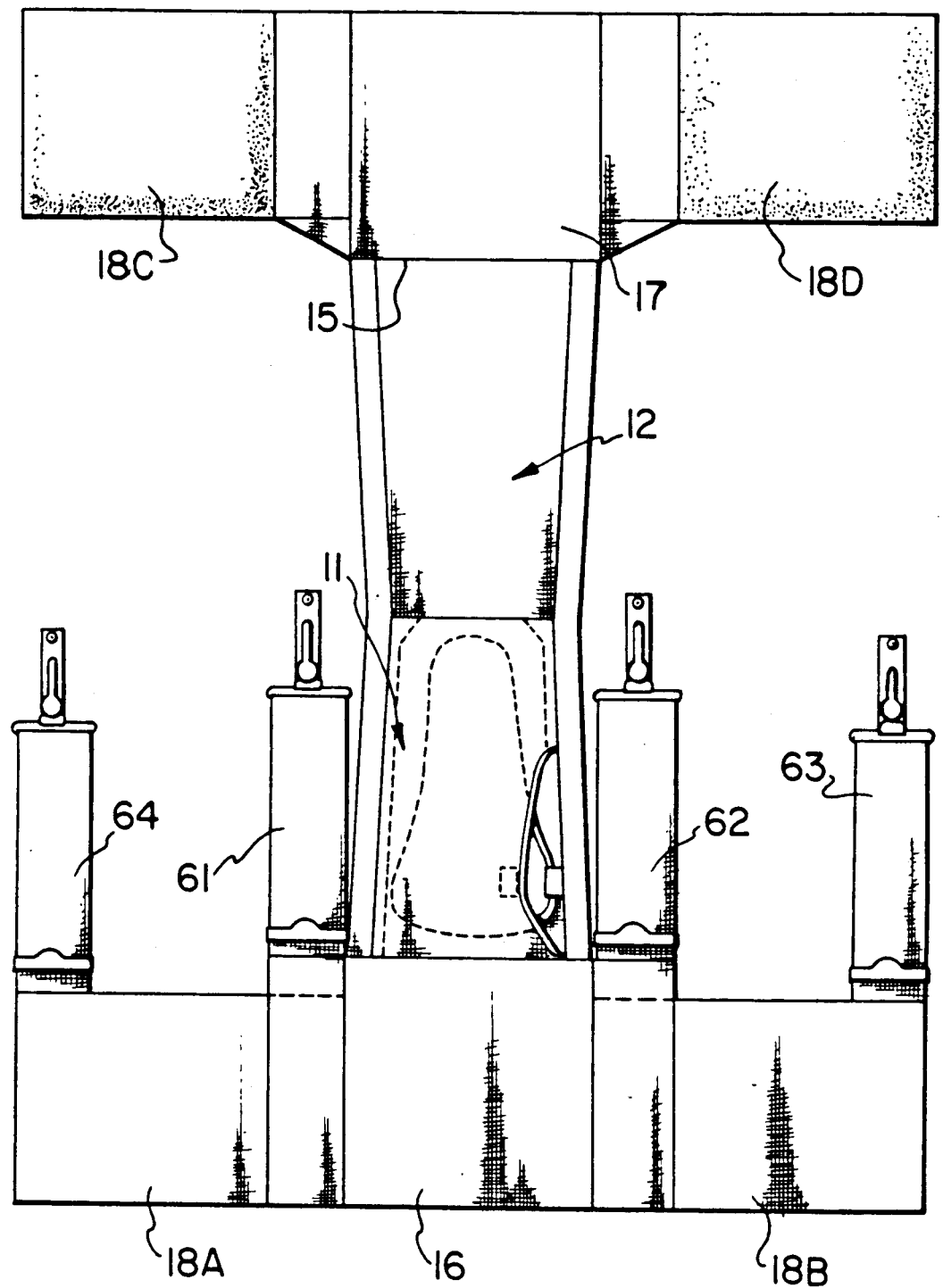
FIG. 3 is the same as FIG. 1, but illustrating the embodiment of FIG. 2 which has garter straps attached to the waistband.

As will be seen from FIGS. 3 and 4, the protective cup 40 has a large upper proportion 41 and a lower, rearwardly curved portion 42. The lower portion is narrower than the upper portion, but if desired a cup of generally rectangular configuration as disclosed in the aforementioned U.S. Pat. No. 3,782,375 could be used with the harness of applicant's particular design.

The preferred cup 40 is illustrated in FIGS. 4 and 5, wherein the upper and lower portions, designated respectively 41 and 42, are detachably interconnected. The detachable connection may consist of variously positioned holes 44 in one (or both) components 41 and 42, and which can be brought into alignment with a hole in the other providing various different positions changing the longitudinal extent of the protector and/or degree of curvature between the two components. The aligned holes receive small bolts 43 with flat nuts on the inner surface or alternatively studs can be threaded into the aligned holes. Alternatively, the two portions of the cup can be provided with mating surfaces that snap together in various different positions. Also the top and/or bottom portions can be provided in different sizes allowing selection of appropriate sized components.

As will be clearly evident from FIGS. 4 and 5, the upper portion of the protective cup has a body engaging outer peripheral surface 46, which, towards the lowered portion thereof, begins to curve rearwardly, aligning with the rearwardly curved body engaging peripheral wall portion 47 of the lower cup part. The body engaging peripheral edge portion of the protective cup can be provided, at least on the lower cup portion, with a soft rubber protective strip 50, similar to that disclosed in the aforementioned U.S. Pat. No. 3,782,375.

In FIGS. 2 and 3, there is illustrated a minor modification wherein there is included garter belt straps, secured to and depending downwardly from the waistband. There may be as many straps as desired, but what is preferred is the arrangement illustrated in FIG. 3 which has four straps 61, 62, 63 and 64, two of which (61 and 62) are fastened to the front elastic band portion 16 and two of which (17 and 18) are secured to the rear face of Velcro fastening bands 18A and 18B. The Velcro bands 18A and 18B extend from the ends of the elastic front band 16.

I claim:

1. An athletic supporter comprising:
   (a) a fabric front and rear panel, separated one from the other by a narrow crotch portion that passes between the wearers legs, said front panel having a front marginal end and said rear panel having a rear marginal end; said panels having opposite marginal edges that extend from one to the other of said opposite ends; said opposite marginal edges of the front and rear panels being made of a stretchable material;
   (b) first and second portions of an elastic waistband, secured respectively to said front and rear marginal ends of said panels;
   (c) means detachably connecting opposite ends of said first waistband portion with adjacent opposite ends of said second waistband portion;
   (d) a pouch on said front panel with an open edge portion for removably receiving therein a rigid protective cup; and
   (e) a rigid protective cup having an upper portion and a lower, rearwardly curved portion and wherein said lower portion is adjustably secured to said upper portion to selectively vary the degree of arcuate curvature of said lower portion relative to said upper portion.

2. An athletic supporter as defined in claim 1, wherein each of said opposite marginal edges of the front and rear panels have an elastic strip secured thereto.

3. An athletic supporter as defined in claim 1, wherein said means detachably connecting opposite ends of the waistband portion portions comprise hook and loop fastening means.

4. An athletic supporter as defined in claim 1, wherein said elastic waistband portions have a width of three to four inches.

5. An athletic supporter as defined in claim 1, including garter straps secured to and suspended from the elastic waistband portions.

6. A jock strap having a front panel, a pouch on said front panel with an open edge for removably receiving therein a rigid protective cup and a rigid protective cup removably insertable into said pouch, said protective cup having an upper portion and a lower, rearwardly curved portion and wherein said lower portion is adjustably secured to said upper portion to selectively vary the degree of arcuate curvature of said lower portion relative to said upper portion.

7. A jock strap and protective cup as defined in claim 6 wherein the lower portion of said protective cup is substantially narrower than the upper part and curves rearwardly to fit partially between the legs of the wearer and said lower portion is adjustably secured to said upper portion to selectively vary the longiudinal length of said protective cup.

8. An athletic supporter as defined in claim 6, including garter straps secured thereto.

* * * * *